(12) United States Patent
Yoshihara et al.

(10) Patent No.: US 11,479,757 B2
(45) Date of Patent: Oct. 25, 2022

(54) MODIFIED SARCOSINE OXIDASE, AND GENE AND PRODUCTION METHOD THEREFOR

(71) Applicant: KIKKOMAN CORPORATION, Noda (JP)

(72) Inventors: Eriko Yoshihara, Noda (JP); Keisuke Furukawa, Noda (JP); Kazuhiko Shimoji, Noda (JP)

(73) Assignee: KIKKOMAN CORPORATION, Noda (JP)

( * ) Notice: Subject to any disclaimer, the term of this patent is extended or adjusted under 35 U.S.C. 154(b) by 409 days.

(21) Appl. No.: 16/332,720

(22) PCT Filed: Sep. 13, 2017

(86) PCT No.: PCT/JP2017/032992
§ 371 (c)(1),
(2) Date: Mar. 12, 2019

(87) PCT Pub. No.: WO2018/052005
PCT Pub. Date: Mar. 22, 2018

(65) Prior Publication Data
US 2019/0218528 A1   Jul. 18, 2019

(30) Foreign Application Priority Data

Sep. 15, 2016 (JP) .............................. JP2016-180796

(51) Int. Cl.
*C12N 9/06* (2006.01)
*C12Q 1/26* (2006.01)
*C12Q 1/34* (2006.01)
*G01N 33/70* (2006.01)
*C12N 5/10* (2006.01)

(52) U.S. Cl.
CPC ............. *C12N 9/0034* (2013.01); *C12N 5/10* (2013.01); *C12Q 1/26* (2013.01); *C12Q 1/34* (2013.01); *C12Y 105/03001* (2013.01); *G01N 33/70* (2013.01)

(58) Field of Classification Search
None
See application file for complete search history.

(56) References Cited

U.S. PATENT DOCUMENTS

| 4,216,292 A | 8/1980 | Ikuta et al. |
| 5,024,945 A | 6/1991 | Mayr et al. |
| 6,228,626 B1 | 5/2001 | Ichikawa et al. |

(Continued)

FOREIGN PATENT DOCUMENTS

| CN | 101407795 | * | 4/2009 |
| JP | S54-52789 | | 4/1979 |
| JP | S56-92790 | | 7/1981 |

(Continued)

OTHER PUBLICATIONS

Nishiya et al., J. Anal. Bio-Sci. 33(2): 161-166 (2010).*

(Continued)

*Primary Examiner* — Erin M. Bowers
(74) *Attorney, Agent, or Firm* — Lucas & Mercanti, LLP

(57) ABSTRACT

To reduce the effect of L-proline in the reaction of a sarcosine oxidase. A modified sarcosine oxidase having reduced reactivity to L-proline is provided.

8 Claims, 5 Drawing Sheets

Specification includes a Sequence Listing.

(56) References Cited

U.S. PATENT DOCUMENTS

2006/0051832 A1   3/2006   Kishimoto et al.

FOREIGN PATENT DOCUMENTS

| JP | S60-43379   | 3/1985  |
|----|-------------|---------|
| JP | H02-265478  | 10/1990 |
| JP | H05-115281  | 5/1993  |
| JP | H10-248572  | 9/1998  |
| JP | 2000-175685 | 6/2000  |
| JP | 2004159566  | 6/2004  |
| JP | 2009055919  | 3/2009  |
| JP | 2009072196  | 4/2009  |

OTHER PUBLICATIONS

Nishiya et al., "Alteration of L-proline oxidase activity of Sarcosine oxidase and a structural interpretation", Journal of Analytical Bio-Science, vol. 33, No. 2, 2010, pp. 161-166.
Suzuki, "Purification and Some Properties of Sarcosine Oxidase from *Corynebacterium* sp. U-96", J. Biochem. Vol. 89, No. 2, 1981, pp. 599-607.

\* cited by examiner

SEQUENCE LISTING

```
<160> NUMBER OF SEQ ID NOS: 24

<210> SEQ ID NO 1
<211> LENGTH: 387
<212> TYPE: PRT
<213> ORGANISM: Bacillus sp. NS-129

<400> SEQUENCE: 1

Met Ser Thr His Phe Asp Val Ile Val Val Gly Ala Gly Ser Met Gly
1               5                   10                  15

Met Ala Ala Gly Tyr Tyr Leu Ala Lys Gln Gly Val Lys Thr Leu Leu
            20                  25                  30

Val Asp Ser Phe Asp Pro Pro His Thr Asn Gly Ser His His Gly Asp
        35                  40                  45

Thr Arg Ile Ile Arg His Ala Tyr Gly Glu Gly Arg Glu Tyr Val Pro
    50                  55                  60

Phe Ala Leu Arg Ala Gln Glu Leu Trp Tyr Glu Leu Glu Lys Glu Thr
65                  70                  75                  80

His His Lys Ile Phe Thr Gln Thr Gly Val Leu Val Tyr Gly Pro Lys
                85                  90                  95

Gly Gly Ser Ala Phe Val Ser Glu Thr Met Glu Ala Ala Asn Ile His
            100                 105                 110
```

```
Ser Leu Glu His Glu Leu Phe Glu Gly Lys Gln Leu Thr Asp Arg Trp
            115                 120                 125

Ala Gly Val Glu Val Pro Asp Asn Tyr Glu Ala Ile Phe Glu Pro Asn
        130                 135                 140

Ser Gly Val Leu Phe Ser Glu Asn Cys Ile Gln Ala Tyr Arg Glu Leu
145                 150                 155                 160

Ala Glu Ala His Gly Ala Thr Val Leu Thr Tyr Thr Pro Val Glu Asp
                165                 170                 175

Phe Glu Val Thr Glu Asp Leu Val Thr Ile Lys Thr Ala Lys Gly Ser
            180                 185                 190

Tyr Thr Ala Asn Lys Leu Val Val Ser Met Gly Ala Trp Asn Ser Lys
        195                 200                 205

Leu Leu Ser Lys Leu Asp Val Glu Ile Pro Leu Gln Pro Tyr Arg Gln
210                 215                 220

Val Val Gly Phe Phe Glu Cys Asp Glu Ala Lys Tyr Ser Asn Asn Ala
225                 230                 235                 240

His Tyr Pro Ala Phe Met Val Glu Val Glu Asn Gly Ile Tyr Tyr Gly
                245                 250                 255

Phe Pro Ser Phe Gly Gly Ser Gly Leu Lys Ile Gly Tyr His Ser Tyr
            260                 265                 270

Gly Gln Gln Ile Asp Pro Asp Thr Ile Asn Arg Glu Phe Gly Ala Tyr
        275                 280                 285

Pro Glu Asp Glu Ala Asn Leu Arg Lys Phe Leu Glu Gln Tyr Met Pro
290                 295                 300

Gly Ala Asn Gly Glu Leu Lys Lys Gly Ala Val Cys Met Tyr Thr Lys
305                 310                 315                 320

Thr Pro Asp Glu His Phe Val Ile Asp Leu His Pro Lys Tyr Ser Asn
                325                 330                 335

Val Ala Ile Ala Ala Gly Phe Ser Gly His Gly Phe Lys Phe Ser Ser
            340                 345                 350

Val Val Gly Glu Thr Leu Ala Gln Leu Ala Thr Thr Gly Lys Thr Glu
        355                 360                 365

His Asp Ile Ser Ile Phe Ser Leu Asn Arg Asp Ala Leu Lys Lys Glu
370                 375                 380

Ala Val Lys
385

<210> SEQ ID NO 2
<211> LENGTH: 387
<212> TYPE: PRT
<213> ORGANISM: Bacillus sp. NS-129

<400> SEQUENCE: 2

Met Ser Thr His Phe Asp Val Ile Val Val Gly Ala Gly Ser Met Gly
1               5                   10                  15

Met Ala Ala Gly Tyr Tyr Leu Ala Lys Gln Gly Val Lys Thr Leu Leu
            20                  25                  30

Val Asp Ser Phe Asp Pro Pro His Thr Asn Gly Ser His His Gly Asp
        35                  40                  45

Thr Arg Ile Ile Arg His Ala Tyr Gly Glu Gly Arg Glu Tyr Val Pro
    50                  55                  60

Phe Ala Leu Arg Ala Gln Glu Leu Trp Tyr Glu Leu Glu Lys Glu Thr
65                  70                  75                  80

His His Lys Ile Phe Thr Gln Thr Gly Val Leu Val Tyr Gly Pro Lys
                85                  90                  95
```

Gly Gly Ser Ala Phe Val Ser Glu Thr Met Glu Ala Ala Asn Ile His
            100                 105                 110

Ser Leu Glu His Glu Leu Phe Glu Gly Lys Gln Leu Thr Asp Arg Trp
        115                 120                 125

Ala Gly Val Glu Val Pro Asp Asn Tyr Glu Ala Ile Phe Glu Pro Asn
130                 135                 140

Ser Gly Val Leu Phe Ser Glu Asn Cys Ile Gln Ala Tyr Arg Glu Leu
145                 150                 155                 160

Ala Glu Ala His Gly Ala Thr Val Leu Thr Tyr Thr Pro Val Glu Asp
                165                 170                 175

Phe Glu Val Thr Glu Asp Leu Val Thr Ile Lys Thr Ala Lys Gly Ser
            180                 185                 190

Tyr Thr Ala Asn Lys Leu Val Val Ser Met Gly Ala Trp Asn Ser Lys
        195                 200                 205

Leu Leu Ser Lys Leu Asp Val Glu Ile Pro Leu Gln Pro His Arg Gln
210                 215                 220

Val Val Gly Phe Phe Glu Cys Asp Glu Ala Lys Tyr Ser Asn Asn Ala
225                 230                 235                 240

His Tyr Pro Ala Phe Met Val Glu Val Glu Asn Gly Ile Tyr Tyr Gly
                245                 250                 255

Phe Pro Ser Phe Gly Gly Ser Gly Leu Lys Ile Gly Tyr His Ser Tyr
            260                 265                 270

Gly Gln Gln Ile Asp Pro Asp Thr Ile Asn Arg Glu Phe Gly Ala Tyr
        275                 280                 285

Pro Glu Asp Glu Ala Asn Leu Arg Lys Phe Leu Glu Gln Tyr Met Pro
290                 295                 300

Gly Ala Asn Gly Glu Leu Lys Lys Gly Ser Val Cys Met Tyr Thr Asn
305                 310                 315                 320

Thr Pro Asp Gly His Phe Val Ile Asp Leu His Pro Lys Tyr Ser Asn
                325                 330                 335

Val Ala Ile Ala Ala Gly Phe Ser Gly His Gly Tyr Lys Phe Ser Ser
            340                 345                 350

Val Val Gly Glu Thr Leu Ala Gln Leu Ala Thr Thr Gly Lys Thr Glu
        355                 360                 365

His Asp Ile Ser Ile Phe Ser Leu Asn Arg Asp Ala Leu Lys Lys Glu
370                 375                 380

Ala Val Lys
385

<210> SEQ ID NO 3
<211> LENGTH: 387
<212> TYPE: PRT
<213> ORGANISM: Bacillus sp. NS-129

<400> SEQUENCE: 3

Met Ser Thr His Phe Asp Val Ile Val Val Gly Ala Gly Ser Met Gly
1               5                   10                  15

Met Ala Ala Gly Tyr Tyr Leu Ala Lys Gln Gly Val Lys Thr Leu Leu
            20                  25                  30

Val Asp Ser Phe Asp Pro Pro His Thr Asn Gly Ser His Gly Asp
        35                  40                  45

Thr Arg Ile Ile Arg His Ala Tyr Gly Glu Gly Arg Glu Tyr Val Pro
50                  55                  60

Phe Ala Leu Arg Ala Gln Glu Leu Trp Tyr Glu Leu Glu Lys Glu Thr

```
                65                  70                  75                  80
His His Lys Ile Phe Thr Gln Thr Gly Val Leu Val Tyr Gly Pro Lys
                    85                  90                  95

Gly Gly Ser Ala Phe Val Ser Glu Thr Met Glu Ala Ala Asn Ile His
            100                 105                 110

Ser Leu Glu His Glu Leu Phe Glu Gly Lys Gln Leu Thr Asp Arg Trp
        115                 120                 125

Ala Gly Val Glu Val Pro Asp Asn Tyr Glu Ala Ile Phe Glu Pro Asn
    130                 135                 140

Ser Gly Val Leu Phe Ser Glu Asn Cys Ile Gln Ala Tyr Arg Glu Leu
145                 150                 155                 160

Ala Glu Ala His Gly Ala Thr Val Leu Thr Tyr Thr Pro Val Glu Asp
                165                 170                 175

Phe Glu Val Thr Glu Asp Leu Val Thr Ile Lys Thr Ala Lys Gly Ser
            180                 185                 190

Tyr Thr Ala Asn Lys Leu Val Val Ser Met Gly Ala Trp Asn Ser Lys
        195                 200                 205

Leu Leu Ser Lys Leu Asp Val Glu Ile Pro Leu Gln Pro Tyr Arg Gln
    210                 215                 220

Val Val Gly Phe Phe Glu Cys Asp Glu Ala Lys Tyr Ser Asn Asn Ala
225                 230                 235                 240

His Tyr Pro Ala Phe Met Val Glu Val Glu Asn Gly Ile Tyr Tyr Gly
                245                 250                 255

Phe Pro Ser Ile Gly Gly Ser Gly Leu Lys Ile Gly Tyr His Ser Tyr
            260                 265                 270

Gly Gln Gln Ile Asp Pro Asp Thr Ile Asn Arg Glu Phe Gly Ala Tyr
        275                 280                 285

Pro Glu Asp Glu Ala Asn Leu Arg Lys Phe Leu Glu Gln Tyr Met Pro
    290                 295                 300

Gly Ala Asn Gly Glu Leu Lys Lys Gly Ala Val Cys Met Tyr Thr Asn
305                 310                 315                 320

Thr Pro Asp Gly His Phe Val Ile Asp Leu His Pro Lys Tyr Ser Asn
                325                 330                 335

Val Ala Ile Ala Ala Gly Phe Ser Gly His Gly Phe Lys Phe Ser Ser
            340                 345                 350

Val Val Gly Glu Thr Leu Ala Gln Leu Ala Thr Thr Gly Lys Thr Glu
        355                 360                 365

His Asp Ile Ser Ile Phe Ser Leu Asn Arg Asp Ala Leu Lys Lys Glu
    370                 375                 380

Ala Val Lys
385

<210> SEQ ID NO 4
<211> LENGTH: 387
<212> TYPE: PRT
<213> ORGANISM: Bacillus sp. NS-129

<400> SEQUENCE: 4

Met Ser Thr His Phe Asp Val Ile Val Val Gly Ala Gly Ser Met Gly
1               5                   10                  15

Met Ala Ala Gly Tyr Tyr Leu Ala Lys Gln Gly Val Lys Thr Leu Leu
            20                  25                  30

Val Asp Ser Phe Asp Pro Pro Thr His Gly Ser His Gly Asp
        35                  40                  45
```

```
Thr Arg Ile Ile Arg His Ala Tyr Gly Glu Gly Arg Glu Tyr Val Pro
 50                  55                  60

Phe Ala Leu Arg Ala Gln Glu Leu Trp Tyr Glu Leu Glu Lys Glu Thr
 65                  70                  75                  80

His His Lys Ile Phe Thr Gln Thr Gly Val Leu Val Tyr Gly Pro Lys
                 85                  90                  95

Gly Gly Ser Ala Phe Val Ser Glu Thr Met Glu Ala Ala Asn Ile His
                100                 105                 110

Ser Leu Glu His Glu Leu Phe Glu Gly Lys Gln Leu Thr Asp Arg Trp
            115                 120                 125

Ala Gly Val Glu Val Pro Asp Asn Tyr Glu Ala Ile Phe Glu Pro Asn
130                 135                 140

Ser Gly Val Leu Phe Ser Glu Asn Cys Ile Gln Ala Tyr Arg Glu Leu
145                 150                 155                 160

Ala Glu Ala His Gly Ala Thr Val Leu Thr Tyr Thr Pro Val Glu Asp
                165                 170                 175

Phe Glu Val Thr Glu Asp Leu Val Thr Ile Lys Thr Ala Lys Gly Ser
            180                 185                 190

Tyr Thr Ala Asn Lys Leu Val Val Ser Met Gly Ala Trp Asn Ser Lys
        195                 200                 205

Leu Leu Ser Lys Leu Asp Val Glu Ile Pro Leu Gln Pro Ala Arg Gln
210                 215                 220

Val Val Gly Phe Phe Glu Cys Asp Glu Ala Lys Tyr Ser Asn Asn Ala
225                 230                 235                 240

His Tyr Pro Ala Phe Met Val Glu Val Glu Asn Gly Ile Tyr Tyr Gly
                245                 250                 255

Phe Pro Ser Ile Gly Gly Ser Gly Leu Lys Ile Gly Tyr His Ser Tyr
            260                 265                 270

Gly Gln Gln Ile Asp Pro Asp Thr Ile Asn Arg Glu Phe Gly Ala Tyr
        275                 280                 285

Pro Glu Asp Glu Ala Asn Leu Arg Lys Phe Leu Glu Gln Tyr Met Pro
290                 295                 300

Gly Ala Asn Gly Glu Leu Lys Lys Gly Ala Val Cys Met Tyr Thr Asn
305                 310                 315                 320

Thr Pro Asp Gly His Phe Val Ile Asp Leu His Pro Lys Tyr Ser Asn
                325                 330                 335

Val Ala Ile Ala Ala Gly Phe Ser Gly His Gly Phe Lys Phe Ser Ser
            340                 345                 350

Val Val Gly Glu Thr Leu Ala Gln Leu Ala Thr Thr Gly Lys Thr Glu
        355                 360                 365

His Asp Ile Ser Ile Phe Ser Leu Asn Arg Asp Ala Leu Lys Lys Glu
370                 375                 380

Ala Val Lys
385

<210> SEQ ID NO 5
<211> LENGTH: 21
<212> TYPE: DNA
<213> ORGANISM: Artificial
<220> FEATURE:
<223> OTHER INFORMATION: primer

<400> SEQUENCE: 5
atgagcacgc attttgacgt a                                          21
```

```
<210> SEQ ID NO 6
<211> LENGTH: 30
<212> TYPE: DNA
<213> ORGANISM: Artificial
<220> FEATURE:
<223> OTHER INFORMATION: primer

<400> SEQUENCE: 6
ttattttact gcttcttttt ttaatgcatc                              30

<210> SEQ ID NO 7
<211> LENGTH: 27
<212> TYPE: DNA
<213> ORGANISM: Artificial
<220> FEATURE:
<223> OTHER INFORMATION: primer

<400> SEQUENCE: 7
caaccagcac gtcaagtagt aggattc                                 27

<210> SEQ ID NO 8
<211> LENGTH: 26
<212> TYPE: DNA
<213> ORGANISM: Artificial
<220> FEATURE:
<223> OTHER INFORMATION: primer

<400> SEQUENCE: 8
ttgacgtgct ggttgtaatg gaattt                                  26

<210> SEQ ID NO 9
<211> LENGTH: 27
<212> TYPE: DNA
<213> ORGANISM: Artificial
<220> FEATURE:
<223> OTHER INFORMATION: primer

<400> SEQUENCE: 9
caaccacacc gtcaagtagt aggattc                                 27

<210> SEQ ID NO 10
<211> LENGTH: 26
<212> TYPE: DNA
<213> ORGANISM: Artificial
<220> FEATURE:
<223> OTHER INFORMATION: primer

<400> SEQUENCE: 10
ttgacggtgt ggttgtaatg gaattt                                  26

<210> SEQ ID NO 11
<211> LENGTH: 25
<212> TYPE: DNA
<213> ORGANISM: Artificial
<220> FEATURE:
<223> OTHER INFORMATION: primer

<400> SEQUENCE: 11
ggattcccaa gcattggcgg aagcg                                   25

<210> SEQ ID NO 12
<211> LENGTH: 25
<212> TYPE: DNA
<213> ORGANISM: Artificial
<220> FEATURE:
<223> OTHER INFORMATION: primer
```

```
<400> SEQUENCE: 12
cgcttccgcc aatgcttggg aatcc                                           25

<210> SEQ ID NO 13
<211> LENGTH: 24
<212> TYPE: DNA
<213> ORGANISM: Artificial
<220> FEATURE:
<223> OTHER INFORMATION: primer

<400> SEQUENCE: 13
ctgaaaaaag gctcagtttg catg                                            24

<210> SEQ ID NO 14
<211> LENGTH: 24
<212> TYPE: DNA
<213> ORGANISM: Artificial
<220> FEATURE:
<223> OTHER INFORMATION: primer

<400> SEQUENCE: 14
catgcaaact gagcctttt tcag                                             24

<210> SEQ ID NO 15
<211> LENGTH: 29
<212> TYPE: DNA
<213> ORGANISM: Artificial
<220> FEATURE:
<223> OTHER INFORMATION: primer

<400> SEQUENCE: 15
gtatactaac actccagatg agcactttg                                       29

<210> SEQ ID NO 16
<211> LENGTH: 27
<212> TYPE: DNA
<213> ORGANISM: Artificial
<220> FEATURE:
<223> OTHER INFORMATION: primer

<400> SEQUENCE: 16
ctggagtgtt agtatacatg caaactg                                         27

<210> SEQ ID NO 17
<211> LENGTH: 27
<212> TYPE: DNA
<213> ORGANISM: Artificial
<220> FEATURE:
<223> OTHER INFORMATION: primer

<400> SEQUENCE: 17
ccagatgggc actttgtaat tgactta                                         27

<210> SEQ ID NO 18
<211> LENGTH: 30
<212> TYPE: DNA
<213> ORGANISM: Artificial
<220> FEATURE:
<223> OTHER INFORMATION: primer

<400> SEQUENCE: 18
aaagtgccca tctggagtct tagtatacat                                      30

<210> SEQ ID NO 19
<211> LENGTH: 28
```

<212> TYPE: DNA
<213> ORGANISM: Artificial
<220> FEATURE:
<223> OTHER INFORMATION: primer

<400> SEQUENCE: 19
ctctggacat ggatataaat tctcaagc                                            28

<210> SEQ ID NO 20
<211> LENGTH: 28
<212> TYPE: DNA
<213> ORGANISM: Artificial
<220> FEATURE:
<223> OTHER INFORMATION: primer

<400> SEQUENCE: 20
gcttgagaat ttatatccat gtccagag                                            28

<210> SEQ ID NO 21
<211> LENGTH: 29
<212> TYPE: DNA
<213> ORGANISM: Artificial
<220> FEATURE:
<223> OTHER INFORMATION: primer

<400> SEQUENCE: 21
gtatactaac actccagatg ggcactttg                                           29

<210> SEQ ID NO 22
<211> LENGTH: 387
<212> TYPE: PRT
<213> ORGANISM: Bacillus sp. NS-129

<400> SEQUENCE: 22

Met Ser Thr His Phe Asp Val Ile Val Val Gly Ala Gly Ser Met Gly
1               5                   10                  15

Met Ala Ala Gly Tyr Tyr Leu Ala Lys Gln Gly Val Lys Thr Leu Leu
            20                  25                  30

Val Asp Ser Phe Asp Pro Pro His Thr Asn Gly Ser His His Gly Asp
        35                  40                  45

Thr Arg Ile Ile Arg His Ala Tyr Gly Glu Gly Arg Glu Tyr Val Pro
    50                  55                  60

Phe Ala Leu Arg Ala Gln Glu Leu Trp Tyr Glu Leu Glu Lys Glu Thr
65                  70                  75                  80

His His Lys Ile Phe Thr Gln Thr Gly Val Leu Val Tyr Gly Pro Lys
                85                  90                  95

Gly Gly Ser Ala Phe Val Ser Glu Thr Met Glu Ala Ala Asn Ile His
            100                 105                 110

Ser Leu Glu His Glu Leu Phe Glu Gly Lys Gln Leu Thr Asp Arg Trp
        115                 120                 125

Ala Gly Val Glu Val Pro Asp Asn Tyr Glu Ala Ile Phe Glu Pro Asn
    130                 135                 140

Ser Gly Val Leu Phe Ser Glu Asn Cys Ile Gln Ala Tyr Arg Glu Leu
145                 150                 155                 160

Ala Glu Ala His Gly Ala Thr Val Leu Thr Tyr Thr Pro Val Glu Asp
                165                 170                 175

Phe Glu Val Thr Glu Asp Leu Val Thr Ile Lys Thr Ala Lys Gly Ser
            180                 185                 190

Tyr Thr Ala Asn Lys Leu Val Val Ser Met Gly Ala Trp Asn Ser Lys
        195                 200                 205

```
Leu Leu Ser Lys Leu Asp Val Glu Ile Pro Leu Gln Pro His Arg Gln
    210                 215                 220
Val Val Gly Phe Phe Glu Cys Asp Glu Ala Lys Tyr Ser Asn Asn Ala
225                 230                 235                 240
His Tyr Pro Ala Phe Met Val Glu Val Glu Asn Gly Ile Tyr Tyr Gly
                245                 250                 255
Phe Pro Ser Phe Gly Gly Ser Gly Leu Lys Ile Gly Tyr His Ser Tyr
                260                 265                 270
Gly Gln Gln Ile Asp Pro Asp Thr Ile Asn Arg Glu Phe Gly Ala Tyr
        275                 280                 285
Pro Glu Asp Glu Ala Asn Leu Arg Lys Phe Leu Glu Gln Tyr Met Pro
        290                 295                 300
Gly Ala Asn Gly Glu Leu Lys Lys Gly Ser Val Cys Met Tyr Thr Asn
305                 310                 315                 320
Thr Pro Asp Gly His Phe Val Ile Asp Leu His Pro Lys Tyr Ser Asn
                325                 330                 335
Val Ala Ile Ala Ala Gly Gly Ser Gly His Gly Phe Lys Phe Ser Ser
                340                 345                 350
Val Val Gly Glu Thr Leu Ala Gln Leu Ala Thr Thr Gly Lys Thr Glu
                355                 360                 365
His Asp Ile Ser Ile Phe Ser Leu Asn Arg Asp Ala Leu Lys Lys Glu
        370                 375                 380
Ala Val Lys
385

<210> SEQ ID NO 23
<211> LENGTH: 30
<212> TYPE: DNA
<213> ORGANISM: Artificial
<220> FEATURE:
<223> OTHER INFORMATION: primer

<400> SEQUENCE: 23
gcagctggtg gttctggaca tggatttaaa                                    30

<210> SEQ ID NO 24
<211> LENGTH: 30
<212> TYPE: DNA
<213> ORGANISM: Artificial
<220> FEATURE:
<223> OTHER INFORMATION: primer

<400> SEQUENCE: 24
atgtccagaa ccaccagctg caattgcaac                                    30
```

MODIFIED SARCOSINE OXIDASE, AND GENE AND PRODUCTION METHOD THEREFOR

CROSS-REFERENCE TO RELATED APPLICATIONS

This application is a 371 of PCT/JP2017/032992, filed Sep. 13, 2017, which claims benefit of Japanese Patent Application No. 2016-180796 filed on Sep. 13, 2016.

TECHNICAL FIELD

The present invention relates to a modified sarcosine oxidase having reduced reactivity to L-proline compared to that of an enzyme prior to modification, a modified sarcosine oxidase gene, and a method for producing a modified sarcosine oxidase.

BACKGROUND ART

Sarcosine oxidase is an enzyme with catalytic action hydrolyzing sarcosine to produce glycine and formaldehyde, can be used in the measurement of creatinine level in human serum or urine, and can be utilized as a diagnostic drug for various diseases including kidney diseases.

Conventionally, sarcosine oxidases are known to be produced from bacterial strains such as the genus *Corynebacterium* (see, e.g., Non Patent Literature 1), the genus *Bacillus* (see, e.g., Patent Literature 1), the genus *Cylindrocarpon* (see, e.g., Patent Literature 2), the genus *Pseudomonas* (see, e.g., Patent Literature 3), and the genus *Arthrobacter* (see, e.g., Patent Literature 4).

Additionally, the present applicant isolated a sarcosine oxidase gene from the genus *Bacillus* and succeeded in expressing a large amount of the enzyme by genetic engineering techniques (see, e.g., Patent Literature 5).

However, sarcosine oxidase is known to react slightly with L-proline, which is an infusion constituent. Accordingly, a sarcosine oxidase less susceptible to the effect of L-proline has been needed in order to measure creatinine or creatine accurately. With regard to sarcosine oxidases having reduced reactivity to L-proline, a modified sarcosine oxidase from *Arthrobacter* sp. TE1826 (Patent Literature 6) and a septuple (seven fold) mutant modified sarcosine oxidase produced by using genetic engineering techniques (see, Patent Literature 7 and the like) are known. However, a sarcosine oxidase having reduced reactivity to L-proline is still needed.

CITATION LIST

Patent Literature

Patent Literature 1: JP Patent Publication (Kokai) No. 54-52789 A (1979)
Patent Literature 2: JP Patent Publication (Kokai) No. 56-92790 A (1981)
Patent Literature 3: JP Patent Publication (Kokai) No. 60-43379 A (1985)
Patent Literature 4: JP Patent Publication (Kokai) No. 2-265478 A (1990)
Patent Literature 5: JP Patent Publication (Kokai) No. 5-115281 A (1993)
Patent Literature 6: JP Patent Publication (Kokai) No. 10-248572 A (JP Patent No. 3904098) (1998)
Patent Literature 7: JP Patent Publication (Kokai) No. 2004-159566 A (JP Patent No. 4419044)

Non Patent Literature

Non Patent Literature 1: J. Biochem., 89, 1981, p. 599

SUMMARY OF THE INVENTION

Technical Problem

An object of the present invention is to provide a sarcosine oxidase having reduced reactivity to L-proline.

Solution to the Problem

The present inventors, in view of the above problems, conducted genetic modification of a *Bacillus*-derived sarcosine oxidase gene (described in JP Patent Publication (Kokoku) No. 6-65303 B (1994)) and, as a result, succeeded in obtaining a sarcosine oxidase having reduced reactivity to L-proline, and completed (accomplished) the present invention.

More specifically, the present invention encompasses the following.

[1] A modified sarcosine oxidase having the following characteristics:

(a) action: hydrolysis of 1 mol of sarcosine to produce 1 mol of glycine and 1 mol of formaldehyde; and (b) substrate specificity: relative activity to L-proline of 0.23% or less when activity to sarcosine is 100%.

[2] A modified sarcosine oxidase selected from the following:

(a) a sarcosine oxidase wherein, when an amino acid sequence of the sarcosine oxidase is aligned with the amino acid sequence of SEQ ID NO: 1, at least one position of the following (i) to (vi) is substituted with the following amino acids, and having reduced relative activity to L-proline, wherein (i) the amino acid at the position corresponding to position 320 in SEQ ID NO: 1 is asparagine, (ii) the amino acid at the position corresponding to position 324 in SEQ ID NO: 1 is glycine, (iii) the amino acid at the position corresponding to position 348 in SEQ ID NO: 1 is tyrosine, (iv) the amino acid at the position corresponding to position 222 in SEQ ID NO: 1 is alanine or histidine, (v) the amino acid at the position corresponding to position 260 in SEQ ID NO: 1 is isoleucine, and/or (vi) the amino acid at the position corresponding to position 314 in SEQ ID NO: 1 is serine, and wherein relative activity to L-proline is reduced relative to the wild type;

(b-1) a protein having one or more amino acid substitutions of (a), comprising an amino acid sequence having 80% or more identity with the amino acid sequence of SEQ ID NO: 1, and having sarcosine oxidase activity with reduced reactivity to L-proline compared to that of a protein prior to modification;

(b-2) a modified sarcosine oxidase that is a protein having one or more amino acid substitutions of (a), comprising an amino acid sequence having 75% or more full-length amino acid sequence identity with the amino acid sequence of SEQ ID NO: 1, and having sarcosine oxidase activity with reduced reactivity to L-proline compared to that of a protein prior to modification, and wherein the homologous region consisting of positions 6 to 86, positions 88 to 92, positions 94 to 97, positions 101 to 102, positions 104 to 109, positions 112 to 114, position 118, positions 120 to 121, positions 127 to 128, positions 130 to 131, positions 133 to 134, positions 136 to 137, positions 139 to 142, positions 144 to 154, positions 156 to 166, positions 168 to 178, positions 181 to 182, position 184, position 186, positions 188 to 189, positions 191 to 192, positions 194 to 195, positions 197 to 213, positions 216 to 233, positions 235 to 238, positions 242 to 249, positions 252 to 262, positions 264 to 270, positions 272 to 274, positions 276 to 286, positions 288 to 292, position 294, positions 296 to 300, positions 302 to 306, positions 308 to 311, positions 313 to 332, positions 335 to 358, positions 360 to 362, positions 364 to 375, positions 377 to 378, and positions 380 to 382 of SEQ ID NO: 1 has 95% or more amino acid sequence identity with the homologous region consisting of positions corresponding respectively to the modified sarcosine oxidase;
(c-1) a protein comprising an amino acid sequence having 80% or more identity with the amino acid sequence of SEQ ID NO: 2, 3, or 4, and having sarcosine oxidase activity having reduced reactivity to L-proline compared to that of a protein prior to modification;
(c-2) a modified sarcosine oxidase that is a protein comprising an amino acid sequence having 75% or more full-length amino acid sequence identity with the amino acid sequence of SEQ ID NO: 2, 3, or 4, and having sarcosine oxidase activity having reduced reactivity to L-proline compared to that of a protein prior to modification, and wherein the homologous region consisting of positions 6 to 86, positions 88 to 92, positions 94 to 97, positions 101 to 102, positions 104 to 109, positions 112 to 114, position 118, positions 120 to 121, positions 127 to 128, positions 130 to 131, positions 133 to 134, positions 136 to 137, positions 139 to 142, positions 144 to 154, positions 156 to 166, positions 168 to 178, positions 181 to 182, position 184, position 186, positions 188 to 189, positions 191 to 192, positions 194 to 195, positions 197 to 213, positions 216 to 233, positions 235 to 238, positions 242 to 249, positions 252 to 262, positions 264 to 270, positions 272 to 274, positions 276 to 286, positions 288 to 292, position 294, positions 296 to 300, positions 302 to 306, positions 308 to 311, positions 313 to 332, positions 335 to 358, positions 360 to 362, positions 364 to 375, positions 377 to 378, and positions 380 to 382 of SEQ ID NO: 1 has 95% or more amino acid sequence identity with the homologous region consisting of positions corresponding respectively to the modified sarcosine oxidase;
(d) a protein comprising the amino acid sequence of SEQ ID NO: 2, 3, 4, or 22; or
(e) a protein comprising an amino acid sequence wherein 1 or several amino acids are deleted, substituted, or added in the amino acid sequence of SEQ ID NO: 2, 3, 4, or 22 at positions other than the positions corresponding to positions 222, 260, 314, 320, 324, 343, and 348 in SEQ ID NO: 1, and having sarcosine oxidase activity with reduced reactivity to L-proline compared to that of a protein prior to modification.
[3] The modified sarcosine oxidase of 1 or 2, wherein the amino acid at the position corresponding to position 320 in the amino acid sequence of SEQ ID NO: 1 is asparagine, and the amino acid at the position corresponding to position 324 in the amino acid sequence of SEQ ID NO: 1 is glycine.
[4] The modified sarcosine oxidase of 3, wherein further the amino acid at the position corresponding to position 348 in SEQ ID NO: 1 is tyrosine.
[5] The modified sarcosine oxidase of 3 or 4, wherein further the amino acid at the position corresponding to position 222 in SEQ ID NO: 1 is alanine or histidine.
[6] The modified sarcosine oxidase of any of 3 to 5, wherein further the amino acid at the position corresponding to position 260 in SEQ ID NO: 1 is isoleucine.
[7] The modified sarcosine oxidase of any of 3 to 6, wherein further the amino acid at the position corresponding to position 314 in SEQ ID NO: 1 is serine.
[8] The modified sarcosine oxidase of any of 3 to 7, wherein further the amino acid at the position corresponding to position 343 in SEQ ID NO: 1 is glycine.
[9] A recombinant DNA comprising a vector comprising a sarcosine oxidase gene encoding the modified sarcosine oxidase of any of 2 to 8.
[10] A transformant or transductant comprising the recombinant DNA of 9.
[11] A method for producing a modified sarcosine oxidase, comprising the step of culturing the transformant or transductant of 10 in a medium and collecting sarcosine oxidase from the culture.
[12] A creatinine measurement reagent comprising the modified sarcosine oxidase of any of 1 to 8.
[13] A method for measuring creatinine using the modified sarcosine oxidase of any of 1 to 8, or the measurement reagent of 12.

The present Description encompasses the content as disclosed in Japanese Patent Application No. 2016-180796, which is a priority document of the present application.

Advantageous Effects of the Invention

The modified sarcosine oxidase of the present invention can be used as a measurement reagent for creatinine or creatine. A reagent which uses the present modified sarcosine oxidase is less susceptible to the effect of L-proline, and thus more accurate measurement is enabled.

DESCRIPTION OF EMBODIMENTS

Figure 1:
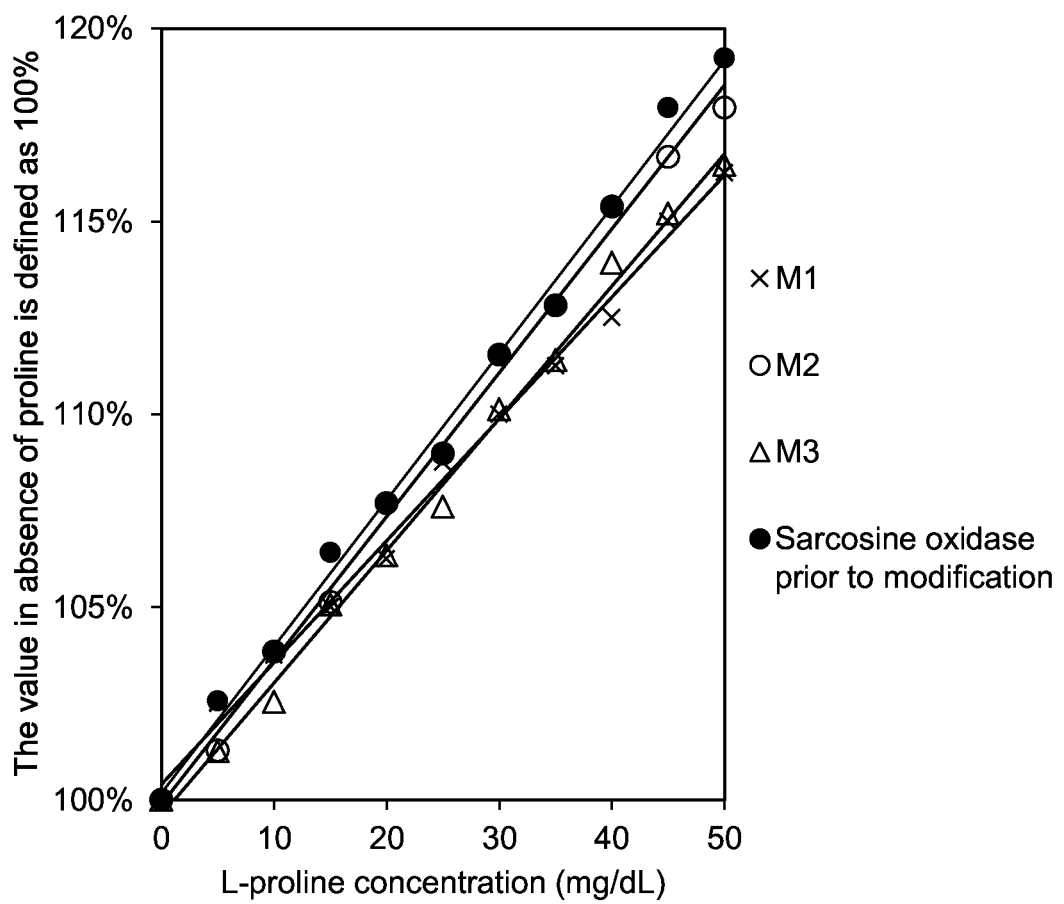
FIG. 1 shows effects of proline on modified sarcosine oxidases and a sarcosine oxidase prior to modification.

The present invention is described in detail as follows.

The sarcosine oxidase of the present invention can be obtained by modifying a gene encoding a sarcosine oxidase. The gene encoding a sarcosine oxidase to be used for modification is not particularly limited, and examples include the genus *Bacillus*-derived sarcosine oxidase gene (described in JP Patent Publication (Kokoku) No. 6-65303 B (1994)). As another example, the sarcosine oxidase gene, may be derived from *Arthrobacter* sp. TE1826 (Journal of Fermentation and Bioengineering, 1993, vol. 75, No. 4, p. 239-244). A vector DNA that can be used in the present invention is not limited. In one embodiment, the vector may be pUTE300K' (described in JP Patent Publication (Kokai) No. 2005-65583 A).

The technique for modifying the genes above may be any known technique, and examples include point mutation (inducing methods) such as a method wherein a chemical mutagen such as hydroxylamine, nitrite or the like is contacted with a sarcosine oxidase expression plasmid containing a sarcosine oxidase gene, e.g., said *Bacillus*-derived sarcosine oxidase gene or a method of random conversion using PCR, a well-known site-specific mutation inducing technique for causing a site-specific substitution or deletion mutation by using a commercial kit; a method wherein the recombinant plasmid DNA is selectively cleaved, and subsequently a selected oligonucleotide is removed or added and ligated; and an oligonucleotide mutation inducing method and the like.

In one embodiment, the modified sarcosine oxidase of the present invention has the following characteristics. That is, the modified sarcosine oxidase of the present invention comprises
(a) action: hydrolysis of 1 mol of sarcosine to produce 1 mol of glycine and 1 mol of formaldehyde, and
(b-1) substrate specificity: relative activity to L-proline of 0.23% or less, 0.22% or less, 0.21% or less, and, for example, 0.20% or less when activity to sarcosine is 100%, and/or
(b-2) substrate specificity: relative activity to L-proline that is 75% or less, 74% or less, and, for example, 73% or less compared with that of a protein prior to modification.

Relative activity to L-proline when activity to sarcosine is (set as) 100% can be determined by setting the absorbance change of a coloring agent when sarcosine is used at a specific concentration (e.g., 95 mM) as the substrate as 100% and measuring the absorbance when the same concentration (e.g., 95 mM) of L-proline is used as the substrate in place of sarcosine.

In one embodiment, the modified sarcosine oxidase of the present invention may be a sarcosine oxidase, wherein
  (i) the amino acid at the position corresponding to position 320 in SEQ ID NO: 1 is asparagine,
  (ii) the amino acid at the position corresponding to position 324 in SEQ ID NO: 1 is glycine,
  (iii) the amino acid at the position corresponding to position 348 in SEQ ID NO: 1 is tyrosine,
  (iv) the amino acid at the position corresponding to position 222 in SEQ ID NO: 1 is alanine or histidine,
  (v) the amino acid at the position corresponding to position 260 in SEQ ID NO: 1 is isoleucine, and/or
  (vi) the amino acid at the position corresponding to position 314 in SEQ ID NO: 1 is serine, and
wherein relative activity to L-proline is reduced relative to the wild type. Optionally, further
  (vii) the amino acid at the position corresponding to position 343 may be glycine. In such a case, the position corresponding to position 348 in SEQ ID NO: 1 may or may not be tyrosine.

In one embodiment, the amino acid at the position corresponding to position 320 in the amino acid sequence of SEQ ID NO: 1 of the modified sarcosine oxidase of the present invention is asparagine, and the amino acid at the position corresponding to position 324 in the amino acid sequence is glycine. In one embodiment, further the amino acid at the position corresponding to position 348 in SEQ ID NO: 1 of the modified sarcosine oxidase of the present invention is tyrosine. In one embodiment, further the amino acid at the position corresponding to position 222 in SEQ ID NO: 1 the modified sarcosine oxidase of the present invention is alanine or histidine. In one embodiment, further the amino acid at the position corresponding to position 260 in SEQ ID NO: 1 of the modified sarcosine oxidase of the present invention is isoleucine. In one embodiment, further the amino acid at the position corresponding to position 314 in SEQ ID NO: 1 of the modified sarcosine oxidase of the present invention is serine. In one embodiment, further the position corresponding to position 343 in SEQ ID NO: 1 of the modified sarcosine oxidase of the present invention may be glycine, and in such a case, the position corresponding to position 348 in SEQ ID NO: 1 may be tyrosine, or may be phenylalanine.

A method for identifying the "position corresponding to" in an amino acid sequence can be carried out by, for example, comparing amino acid sequences using a known algorithm such as Lipman-Pearson method to assign maximum identity to conserved amino acid residues present in the amino acid sequence of each protein. By aligning the amino acid sequences with such method, the positions of homologous amino acid residues in the full-length sequence can be determined regardless of insertions or deletions in the amino acid sequences. Corresponding positions (homologous position) are considered to exist in the same position in the three-dimensional structure and expected to have similar functions in the sarcosine oxidase of interest.

In one embodiment, the modified sarcosine oxidase of the present invention comprises one or more amino acid substitutions of (i) to (vii) above, and further comprises an amino acid sequence having 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% or more identity with the amino acid sequence of SEQ ID NO: 1, and has sarcosine oxidase activity with reduced reactivity to L-proline compared to that of a protein prior to modification.

The identity of amino acid sequences can be calculated using a program such as Maximum Matching or Search Homology of GENETYX (manufactured by GENETYX Corporation), or Maximum Matching or Multiple Alignment of DNASIS Pro (manufactured by Hitachi Solutions, Ltd.), or a multiple alignment of CLUSTAL W. For calculating the amino acid sequence identity, when two or more sarcosine oxidases are aligned, identical amino acid positions in the two or more sarcosine oxidases can be investigated. Using this information, identical regions in the amino acid sequences can be determined. % identity in two or more amino acid sequences herein refers to the percentage obtained by using the total number of amino acids in the regions that can be aligned as the denominator and the number of positions where identical amino acids are present as the numerator when two or more amino acid sequences are aligned using an algorithm such as Blosum62. As such, if there is a region with no identity for two or more amino acid sequences, said region cannot be aligned and typically is not used for the calculation of % identity (identity %).

In the present invention, the region consisting of positions 6 to 86, positions 88 to 92, positions 94 to 97, positions 101 to 102, positions 104 to 109, positions 112 to 114, position 118, positions 120 to 121, positions 127 to 128, positions 130 to 131, positions 133 to 134, positions 136 to 137, positions 139 to 142, positions 144 to 154, positions 156 to 166, positions 168 to 178, positions 181 to 182, position 184, position 186, positions 188 to 189, positions 191 to 192, positions 194 to 195, positions 197 to 213, positions 216 to 233, positions 235 to 238, positions 242 to 249, positions 252 to 262, positions 264 to 270, positions 272 to 274, positions 276 to 286, positions 288 to 292, position 294, positions 296 to 300, positions 302 to 306, positions 308 to 311, positions 313 to 332, positions 335 to 358, positions 360 to 362, positions 364 to 375, positions 377 to 378, and positions 380 to 382 in the amino acid sequence of SEQ ID NO: 1 is termed the "homologous region" of sarcosine oxidase. With regard to the homologous region, when there is no corresponding position, such position is excluded from the calculation of % identity.

In one embodiment, the modified sarcosine oxidase of the present invention comprises one or more amino acid substitutions of (i) to (vii) above, further comprises an amino acid sequence having 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% or more full-length amino acid sequence identity with the amino acid sequence of SEQ ID NO: 1, wherein the homologous region consisting of the above positions in the amino acid sequence of SEQ ID NO: 1 and the homologous region consisting of the corresponding positions, respectively, of the modified sarcosine oxidase have 85%, 86%, 87%, 88%, 89%, 90%, 91%, 92%, 93%, 94%, 95%, 96%, 97%, 98%, or 99% or more amino acid sequence identity, and has sarcosine oxidase activity with reduced reactivity to L-proline compared to that of a protein prior to modification.

Sarcosine oxidase is known to bind to a coenzyme via a specific amino acid sequence motif. In an FAD binding (type) sarcosine oxidase, the motif sequence binding to the coenzyme FAD is Gly-Xaa-Gly-Xaa-Xaa-Gly (wherein Xaa represents any amino acid), which is highly conserved in various FAD binding sarcosine oxidases. This motif sequence appears in the amino acid sequence at the positions corresponding to positions 11 to 16 in SEQ ID NO: 1. Accordingly, in one embodiment, the amino acid sequence of the sarcosine oxidase is Gly-Xaa-Gly-Xaa-Xaa-Gly (wherein Xaa represents any amino acid) at the positions corresponding to positions 11 to 16 in SEQ ID NO: 1.

In one embodiment, the modified sarcosine oxidase of the present invention comprises an amino acid sequence having 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% or more identity with the amino acid sequence of SEQ ID NO: 2, 3, 4, or 22, and has sarcosine oxidase activity with reduced reactivity to L-proline compared to that of a protein prior to modification.

In one embodiment, the modified sarcosine oxidase of the present invention comprises the amino acid sequence of SEQ ID NO: 2, 3, 4, or 22. In one embodiment, the modified sarcosine oxidase of the present invention comprises an amino acid sequence wherein 1 or several amino acids are deleted, substituted, or added in the amino acid sequence of SEQ ID NO: 2, 3, 4, or 22 at positions other than the positions corresponding to positions 222, 260, 314, 320, 324, 343, and 348 in SEQ ID NO: 1, and has sarcosine oxidase activity with reduced reactivity to L-proline compared to that of a protein prior to modification. Several amino acids herein refers to, for example, 10 amino acids, for example, 5 amino acids and 4 amino acids, for example, 3 amino acids.

In one embodiment, the modified sarcosine oxidase of the present invention may further have additional mutations. For example, the amino acid at the position corresponding to position 61 in SEQ ID NO: 1 may be lysine, the amino acid at the position corresponding to position 241 in SEQ ID NO: 1 may be glycine, and/or the amino acid at the position corresponding to position 269 in SEQ ID NO: 1 may be histidine. Additionally, the amino acid at the position corresponding to position 343 in SEQ ID NO: 1 may be glycine.

The vector DNA to be used may be any vector DNA, and may be, for example, plasmid DNA or bacteriophage DNA. In one embodiment, the vector may be pUTE300K' (described in JP Patent Publication (Kokai) No. 2005-65583 A).

Subsequently, the recombinant DNA treated as above is purified using, for example, GenElute Plasmid Miniprep Kit (SIGMA) to obtain various recombinant DNAs.

The thus obtained various recombinant DNAs can be used to transform or transduce, for example, *Escherichia coli* K12, preferably *Escherichia coli* DH5a, *Escherichia coli* JM109 (manufactured by Toyo Boseki Kabushiki Kaisha), or XL1-Blue (manufactured by STRATAGENE), thereby obtaining a transformant or a transductant as a colony containing a recombinant DNA carrying the sarcosine oxidase gene having various mutations introduced thereto. The transformant or transductant carrying various mutations is cultured per each colony, and subsequently disrupted using sonication or a surfactant to obtain a crude enzyme solution of the sarcosine oxidase carrying various mutations.

Subsequently, reactivity to L-proline of the sarcosine oxidase crude enzyme solution of each colony is confirmed. Specifically, the reaction ratio to L-proline and sarcosine (L-proline activity/sarcosine activity) of each crude enzyme solution prepared from each colony is compared with the L-proline activity/sarcosine activity of the wild-type sarcosine oxidase prior to modification, thereby selecting a transformant or transductant having reduced reactivity to L-proline. Additionally, each crude solution prepared from each colony is reacted with diluted sarcosine to confirm changes in the affinity to sarcosine.

The thus obtained superior modified mutants can be cultured in nutrient medium to produce large amounts of modified sarcosine oxidases. Culture medium to be used include those wherein, for example, one or more inorganic salts such as potassium dihydrogenphosphate, potassium hydrogenphosphate, magnesium sulfate, ferric chloride, ferric sulphate, or manganese sulphate is added to one or more nitrogen sources such as a yeast extract, a peptone, a meat extract, a corn steep liquor, a soybean or wheat malt infusion, and further a sugar source and vitamins are added where necessary.

It is appropriate to adjust the initial pH of medium to 7 to 9. Additionally, culture can preferably be carried out at 30 to 42° C., preferably about 37° C., for 6 to 24 hours, by aerated and stirred submerged culture, shaking culture, or stationary culture. After completion of culture, a typical enzyme collection means can be used to collect the sarcosine oxidase from the culture.

The bacterial cell body is separated from the culture by operations such as filtration and centrifugation and the like and then washed. The sarcosine oxidase is preferably collected from this bacterial cell body. In this case, while the bacterial cell body can be used per se, it is preferable to collect the sarcosine oxidase from the bacterial cell body by a method of disrupting the bacterial cell body using various disruption means such as a sonicator, a French press, a dyno-mill and the like, a method of lysing the bacterial cell body wall using a cell-wall lysing enzyme such as lysozyme, or a method of extracting the enzyme from the bacterial cell body using a surfactant such as Triton X-100.

In order to isolate a sarcosine oxidase from the thus obtained crude enzyme solution, a method typically used for enzyme purification can be employed. For example, ammonium sulfate precipitation method, organic solvent precipitation method, ion-exchange chromatography, gel filtration chromatography, adsorption chromatography, and electrophoresis and the like can preferably be carried out in suitable combination.

In one embodiment, a creatinine measurement reagent comprising the modified sarcosine oxidase of the present invention is provided. The creatinine measurement reagent may contain other suitable components or reagents such as a buffer, stabilizer, creatininase, creatinase, peroxidase, and coloring agent. Each of the constituents (components) may be an identical or different reagent. In one embodiment, a method for measuring creatinine using the modified sarcosine oxidase of the present invention or the measurement reagent above is provided. The method for measuring creatinine comprises a step of bringing the modified sarcosine oxidase of the present invention into contact with a sample which may contain sarcosine or a sample wherein sarcosine may be produced by the action of enzyme or the like.

(Enzyme Activity)

The activity of the present enzyme on sarcosine and L-proline can be measured under the following conditions. Incidentally, with regard to sarcosine, enzyme activity which can produce 1 μmol of urea per minute is defined as 1 unit (U).

(Reagent Preparation)

The following solutions are prepared as reagents for reactions.
1) 0.01 M or 0.2 M sarcosine, 100 mM Tris-HCl, 2 mM KCl, 0.1% Triton-X100 (pH 7.7); or 0.2 M L-proline, 100 mM Tris-HCl, 2 mM KCl, 0.1% Triton-X100 (pH 7.7)
2) 80 U/ml POD solution
3) 0.1% TOOS (N-ethyl N-(2-hydroxy-3-sulfopropyl)-3-methylaniline) solution or 0.1% phenol solution
4) 0.2% 4-aminoantipyrine solution
5) Ultrapure water
6) 0.3% SDS solution
7) 20 mM Tris-HCl, 1 mM KCl, 0.2% BSA (pH 7.7) (liquid for diluting enzyme)

Subsequently, the following amounts of the above-mentioned solutions are mixed to prepare an activity measurement liquid.
1) 5 ml
2) 1 ml
3) 2 ml
4) 1 ml
5) 1 ml Measurement can be performed as follows.
1) Pre-incubate 0.95 mL of the activity measurement liquid at 37° C. for 5 minutes.
2) Add and mix 0.05 ml of enzyme solution diluted appropriately to each substrate.
3) React for 10 minutes at 37° C. for sarcosine, and 60 minutes at 37° C. for L-proline.
4) After the reaction for 10 minutes (4.8 mM, 95 mM sarcosine) or the reaction for 60 minutes (95 mM L-proline), mix the 0.3% SDS solution mentioned above to stop (quench) the reaction.
5) Measure the absorbance at 555 nm at 25° C. ($OD_{sample}$).

The blank value is measured by mixing a 0.3% SDS solution before the enzyme solution is mixed ($OD_{blank}$).
6) First confirm the ratio between $\Delta OD_{555\ nm}$ ($OD_{sample} - OD_{blank}$) measured by the reactions with sarcosine at a final concentration of 95 mM and L-proline at a final concentration of 95 mM. Then, calculate the relative activity ratio to that of the wild type (95 mM L-proline activity/95 mM sarcosine activity).

Further, by measuring the 4.8 mM sarcosine activity as well, confirm the affinity (4.8 mM sarcosine activity/95 mM sarcosine activity), and calculate the relative activity ratio to that of the wild type.

In one embodiment, the present invention provides a mutant sarcosine oxidase having K320N/E324G mutations. This is referred to as mutant M0 in the present specification. In another embodiment, the present invention provides mutated sarcosine oxidase M1 (SEQ ID NO: 2). Mutant M1 comprises the K320N/E324G/Y222H/F348Y/A314S mutations. In another embodiment, the present invention provides mutated sarcosine oxidase M2 (SEQ ID NO: 3). Mutant M2 comprises the K320N/E324G/F260I mutations. In another embodiment, the present invention provides mutated sarcosine oxidase M3 (SEQ ID NO: 4). Mutant M3 comprises the K320N/E324G/F260I/Y222A mutations. In another embodiment, the present invention provides the mutant sarcosine oxidase M4 (SEQ ID NO: 22). Mutant M4 comprises the K320N/E324G/Y222H/A314S/F343G mutations. These mutant proteins can be obtained, for example, by appropriately designing primers which introduce the mutations into the wild-type sarcosine oxidase gene, introducing the mutations and expressing the modified gene.

The mutant sarcosine oxidases M0, M1, M2, M3 and M4 can be appropriately purified and formulated for creatinine-measuring reagents. Reactivity to L-proline in a reagent can be evaluated using a serum to which L-proline is added artificially. As for the mutations which constitute the mutant sarcosine oxidases (namely, K320N, E324G, Y222H, Y222A, F348Y, A314S, F260I, and further F343G), the effect per each single mutation can be confirmed with a crude enzyme solution or a purified enzyme. Multiple mutants can be generated where necessary, and effects thereof can be confirmed.

EXAMPLES

The present invention will be described in further detail by the following Examples.

Example 1

*Escherichia coli* (*E. coli*) DH5α (pSON), containing a recombinant plasmid DNA (a vector obtained by incorporating the SON gene of SEQ ID NO: 1 into the vector pUTE300K', hereinafter described as pSON) was cultured in an LB culture medium (manufactured by Difco Laboratories Incorporated), and the bacterial bodies were collected. Subsequently, the recombinant plasmid DNA pSON was extracted and purified therefrom using the GenElute Plasmid Miniprep Kit (Sigma-Aldrich Co. LLC.). The obtained recombinant plasmid was about 100 μg.

Based on the obtained recombinant plasmid, error-prone PCR was carried out using primers for the N-terminus and C-terminus (SEQ ID NOs: 5 and 6). Error-prone PCR was performed using the GeneMorphII EZClone Domain Mutagenesis Kit (manufactured by Agilent Technologies, Inc.). After the reaction, *E. coli* DH5α (manufactured by NIPPON GENE CO., LTD.) was transformed using a library of sarcosine oxidase genes having various mutations introduced, and mutant sarcosine oxidases were produced to obtain a transformant library.

Subsequently, obtained colonies were cultured in 2 ml of a TY culture medium (containing 25 μg/ml kanamycin and 1 mM IPTG). After culturing at 37° C. for 18 to 24 hours, bacterial bodies were collected with centrifugation and the culture medium was replaced with 20 mM Tris-HCl (pH 8.0), 1 mM KCl (pH 7.7), and the bacterial bodies were disrupted using sonication and then centrifuged (at 12000 r.p.m. for 3 minutes).

Activities of the disrupted cell supernatants obtained were measured using sarcosine and L-proline as the substrate. Enzymes having reduced relative activity on proline (95 mM L-proline activity/95 mM sarcosine activity) and having maintained or improved affinity for sarcosine (4.8 mM sarcosine/95 mM sarcosine) compared to those of the enzyme before modification were screened. With regard to error-prone PCR and screening, about 1500 strains were screened in one cycle, and the subsequent error-prone PCR was performed using the plasmids of mutants which had satisfactory results. Three cycles of error-prone PCR→screening was performed.

The superior mutants obtained by screening were subjected to DNA sequencing, and the mutation sites were identified. Effects of single mutations on sarcosine reaction and L-proline reaction were also confirmed. By carrying out the present screening, mutant M1 comprising five mutation sites was first obtained. Moreover, two effective mutations were further confirmed. Next, for each effective mutation, a single mutant was generated, and the effect thereof was confirmed. Primers used for generating the single mutants are as follows (described in order of forward primer and reverse primer, respectively).

Y222A: SEQ ID NOs: 7 and 8
Y222H: SEQ ID NOs: 9 and 10
E324G: SEQ ID NOs: 11 and 12
F348Y: SEQ ID NOs: 13 and 14
F260I: SEQ ID NOs: 15 and 16
A314S: SEQ ID NOs: 17 and 18
K320N: SEQ ID NOs: 19 and 20
K320N/E324G: The forward primer is SEQ ID NO: 21 (the reverse primer is SEQ ID NO: 20).

The results are shown below. The results were obtained using crude enzyme solutions. Incidentally, the reaction was performed using TOOS as the coloring agent.

TABLE 1

Relative activity ratios of single mutants to wild type (%)

| Mutant | 4.8 mM Sar/ 95 mM Sar(%) | 95 mM Pro/ 95 mM Sar(%) | Effect |
|---|---|---|---|
| Wild type | 100 | 100 | |
| Y222A | 94.88 | 69.27 | Reduction of relative activity on L-proline |
| Y222H | 89.64 | 77.76 | Reduction of relative activity on L-proline |
| E324G | 124.06 | 149.29 | Improvement of affinity for sarcosine |
| F348Y | 92.16 | 76.46 | Reduction of relative activity on L-proline |
| F260I | 105.49 | 87.49 | Reduction of relative activity on L-proline, and improvement of affinity for sarcosine |
| A314S | 104.52 | 90.92 | Reduction of relative activity on L-proline, and improvement of affinity for sarcosine |
| K320N | 73.74 | 48.75 | Reduction of relative activity on L-proline |

The relative activity ratios of the single mutants when the relative activity of the sarcosine oxidase prior to modification on substrates were defined as 100% were as in the table, and the effects of each mutation were confirmed.

The superior mutants M0, M2 and M3 were obtained by optionally combining the confirmed mutations based on the result of the reactions to sarcosine and L-proline. These were also generated using the above-mentioned primers. The relative activity ratios of the crude enzyme solutions of mutants M1, M0, M2, and M3 to the wild type are shown in the following table. Incidentally, the present reaction was performed using TOOS as the coloring agent.

TABLE 2

Relative activity ratios of mutants M0, M1, M2 and M3 to wild-type enzyme (%)

| | 4.8 mM Sar/ 95 mM Sar(%) | 95 mM Pro/ 95 mM Sar(%) |
|---|---|---|
| Wild type | 100 | 100 |
| M0 | 84.03 | 49.19 |
| M1 | 92.80 | 44.35 |
| M2 | 90.89 | 46.77 |
| M3 | 107.96 | 52.42 |

With regard to each mutant, while the reactivity to sarcosine was maintained, the reactivity thereof to proline was reduced significantly compared to that of the wild type.

Example 2

Among the mutants obtained as above, *Escherichia coli* (*E. coli*) DH5α comprising the modified sarcosine oxidase gene of M1, M2 or M3 was subjected to shaking culture in 100 ml of a TY culture medium (1% bacto-tryptone, 0.5% bacto-yeast extract, 0.5% NaCl, pH 7.5) containing 25 μg/ml kanamycin at 37° C. for 16 hours. Then, 10 ml of the mixture was inoculated into 7 L of a TY culture medium prepared in the same manner (however, 1 mM of IPTG is included). After the inoculation, this was cultured at a number of revolutions of 120 r.p.m. and 37° C. for about 20 hours.

Step 1 (Preparation of Crude Enzyme Solution)

After culturing, 7 L of the culture solution was passed through a UF membrane (MW 50000), to remove culture medium components and then, was replaced with a 10 mM phosphate buffer with 1 mM EDTA. To this was added EDTA (pH 8.0) to a final concentration of 50 mM, and the mixture was treated with a high-pressure homogenizer to disrupt the bacterial bodies. The disrupted bacterial body liquid was centrifuged, resulting in precipitation of the debris and a crude enzyme solution was obtained.

Step 2 (Ammonium Sulfate Precipitation Treatment)

To 500 ml of the thus obtained crude enzyme was added 20% ammonium sulfate, and ammonium sulfate precipitation was carried out. After ammonium sulfate precipitation, the precipitate was dissolved in a buffer solution comprising 100 mM KCl, 10 mM potassium phosphate buffer solution with 1 mM EDTA and ammonium sulfate was removed by dialyzing against the same buffer as well. Further, the treated liquid subjected to dialysis was centrifuged (at 10,000 g, for 30 minutes) to clarify the crude enzyme solution.

Step 3 (Q Sepharose FF Ion Exchange Chromatography, Batch Type)

The above-mentioned crude enzyme solution (liquid) was adsorbed onto a column loaded with 500 ml of Q Sepharose Fast Flow (trademark, manufactured by GE Healthcare (General Electric Company)) carrier, washed with 1500 ml of a 100 mM KCl, 10 mM potassium phosphate buffer solution including 1 mM EDTA (pH 8.0) and eluted with a 300 mM KCl, 10 mM potassium phosphate buffer solution including 1 mM EDTA (pH 8.0). After the elution, fractions with high degree of purification were collected, concentrated and dialyzed against a 10 mM phosphate buffer solution pH 8.0 containing 150 mM KCl, and 1 mM EDTA.

Step 4 (Q Sepharose FF Ion Exchange Chromatography, Gradient)

A column loaded with 500 ml of a Q Sepharose FF (trademark, manufactured by GE Healthcare) carrier buffered with 10 mM potassium phosphate buffer solution containing 150 mM KCl and 1 mM EDTA was charged with 500 ml of the enzyme solution treated in step 3 and washed with 1500 ml of 10 mM phosphate buffer solution containing 200 mM KCl and 1 mM EDTA. Then, elution was carried out with a 200 mM to 300 mM KCl gradient buffer solution (total liquid volume of 7500 ml) with 10 mM potassium phosphate and 1 mM EDTA and fractions were collected. The collected fractions were analyzed, the fractions having high specific activities (U/OD$_{280\ nm}$) were mixed, and the mixture was dialyzed against a 10 mM potassium phosphate buffer solution pH 8.0 to prepare the enzyme sample.

Example 3

Reactivity of the modified sarcosine oxidases M1, M2 and M3 purified by the method mentioned above and the sarcosine oxidase prior to modification to L-proline were compared using enzyme solutions in which the sarcosine activities were standardized to about 33.0 U/ml. Incidentally, phenol was used as the coloring agent in the present reaction.

The results are shown below. When the relative activity of the sarcosine oxidase prior to modification to substrates is defined as 100%, the relative activity ratio of the modified sarcosine oxidase M1 to L-proline was 51.5%, that of M2 was 73.0%, and that of M3 was 68.7%.

TABLE 3

Relative activity ratios of purified mutants M1, M2 and M3 to wild type (%)

|  | 4.8 mM Sar/ 95 mM Sar(%) | 95 mM Pro/ 95 mM Sar(%) |
| --- | --- | --- |
| Wild type | 100 | 100 |
| M1 | 95.3 | 51.5 |
| M2 | 90.1 | 73.0 |
| M3 | 110.5 | 68.7 |

Example 4

With regard to the modified sarcosine oxidases M1, M2 and M3 purified by the method mentioned above and the sarcosine oxidase prior to modification, when the activity on sarcosine is defined as 100%, the relative activity (%) on L-proline was examined. As for the experimental conditions, with the same procedure as in Example 1, the absorbance, when 95 mM sarcosine was used as the substrate, was defined as 100% and the absorbance, when 95 mM proline was used as the substrate, was evaluated. Phenol was used as the coloring agent. The results are shown below.

TABLE 4

Relative activities of purified mutants M1, M2 and M3 on proline (%)

|  | Relative activity on proline (%) |
| --- | --- |
| Wild type | 0.27 |
| M1 | 0.14 |
| M2 | 0.20 |
| M3 | 0.19 |

Example 5

The degree of the effect of proline when each of the various sarcosine oxidases obtained above was applied to a creatinine measurement reagent was evaluated. The creatinine measurement reagent is as follows.

The following first and second reagents were prepared, and creatinine was measured using a commercial control serum (PreciControlClinChemMulti1, EXA Liquid 3 normal, or Seiken Liquid Normal V) as the sample.

| (First reagent) | |
| --- | --- |
| Ascorbate oxidase | 10 U/mL |
| Catalase | 300 U/mL |
| Creatinase | 35 U/mL |
| Sarcosine oxidase | 11 U/mL |
| TES (2-[[1,3-dihydroxy-2-(hydroxymethyl)propan-2-yl]amino]ethanesulfonic acid) buffer | 20 mM, pH 8.2 |
| N-ethyl-N-(2-hydroxy-3-sulfopropyl-m-toluidine) (TOOS) | 1.0 mM |
| Triton X-100 | 0.1% |
| Potassium chloride | 70 mM |

| (Second reagent) | |
| --- | --- |
| 4-Amino antipyrine | 4.0 mM |
| Creatininase | 370 U/mL |
| Peroxidase | 15 U/mL |
| TES buffer | 20 mM, pH 8.0 |
| Triton X-100 | 0.1% |
| Potassium chloride | 70 mM |
| Sodium azide | 0.09% |

Incidentally, regarding each enzyme, the enzyme activity which produces 1 μmol of product per minute is defined as 1 unit (U) for reach enzyme.

To a control serum as the measurement sample was added L-proline so that the concentrations were 0, 10, 20, 30, 40 and 50 mg/dL. Measurement was initiated by adding 125 μL of the first reagent to 7 μL of the sample. Then, 63.0 μL of the second reagent was added thereto 5 minutes after initiation of the measurement. A BM-1650 automatic-analyzer manufactured by JEOL Ltd. was used for measurement and the measurement wavelength was set with the dominant wavelength=545 nm and sub-wavelength=658 nm. Physiological saline was used as the sample for the reagent blank. The reagent blank and aqueous solutions with known creatinine concentrations were measured beforehand, to prepare a calibration curve, and, based on the same, measured values were determined as the creatinine at the time of sample measurement.

As shown in FIG. 1, the effects of proline on the modified sarcosine oxidases were reduced compared to that on the sarcosine oxidase prior to modification.

Reactivities to 5.0 mg/dL of creatinine were compared using the reagents with the modified sarcosine oxidases and with the sarcosine oxidase prior to modification.

Figure 2:
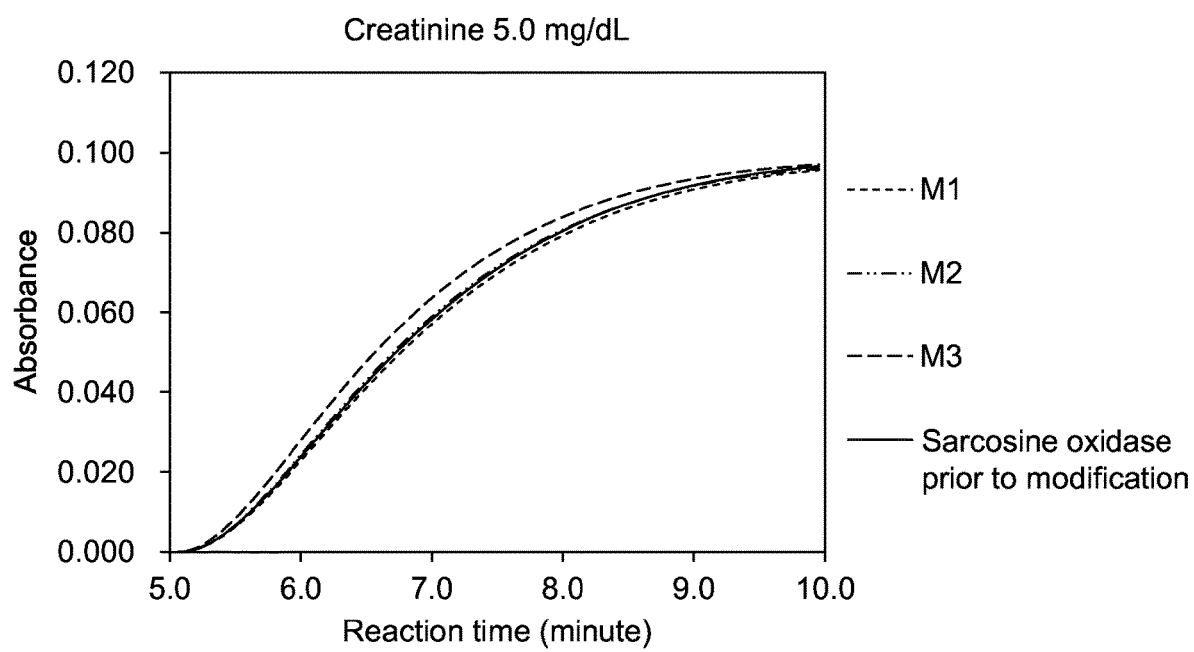
FIG. 2 shows reactivities of a creatinine measurement reagent to which a modified sarcosine oxidase or a sarcosine oxidase prior to modification was added.

As shown in FIG. 2, it was found out that reactivities of the reagents with the modified sarcosine oxidases were the same as that of the reagent with the sarcosine oxidase prior to modification.

As such, it was found that the reactions of the modified sarcosine oxidases are the same as that of the sarcosine oxidase prior to modification, and the effect of proline on the modified sarcosine oxidases is suppressed.

Example 6

Method for Producing M4

Briefly, the modified sarcosine oxidase M4 (SEQ ID NO: 22) having the mutations of K320N/E324G/Y222H/A314S/F343G was generated by PCR with a plasmid comprising SOD-M1 as the template and using the following primers (SEQ ID NOs: 23 and 24).

```
                                            (SEQ ID NO: 23)
        gcagctggtggttctggacatggatttaaa (SEQ ID NO: 24)
        atgtccagaaccaccagctgcaattgcaac
```

The procedure for obtaining the plasmid and PCR conditions were the same as in Example 1. The obtained plasmid DNA was sequenced, and the introduction of the mutations was confirmed.

Method for Evaluating M4

*Escherichia coli* (*E. coli*) DH5α comprising the modified sarcosine oxidase gene M4 was cultured with the same procedure as in Example 2 to prepare a purified enzyme solution. Subsequently, the degree of the effect of proline when the modified sarcosine oxidase M4 was applied to a creatinine measurement reagent was evaluated by the same procedure as in Example 5. The creatinine measurement reagent was the same as that of Example 5. Further, the following serums were used.

PreciControlClinChemMulti1 Lot. 168 332-02
EXA Liquid 3 normal Lot. NL052G
Seiken Liquid Normal V Lot. VNO10103

Figure 3:
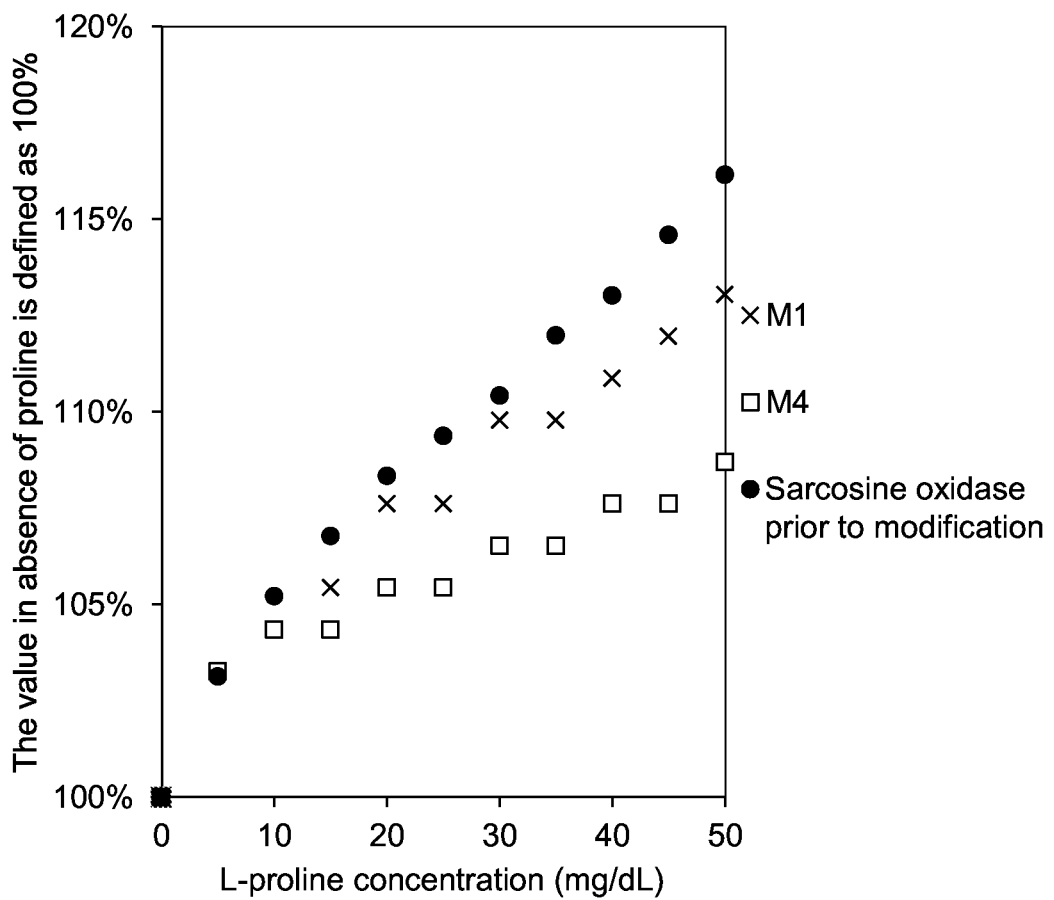
FIG. 3 shows effects of proline on modified sarcosine oxidases and a sarcosine oxidase prior to modification (serum: PreciControlClinChemMulti1).
Figure 4:
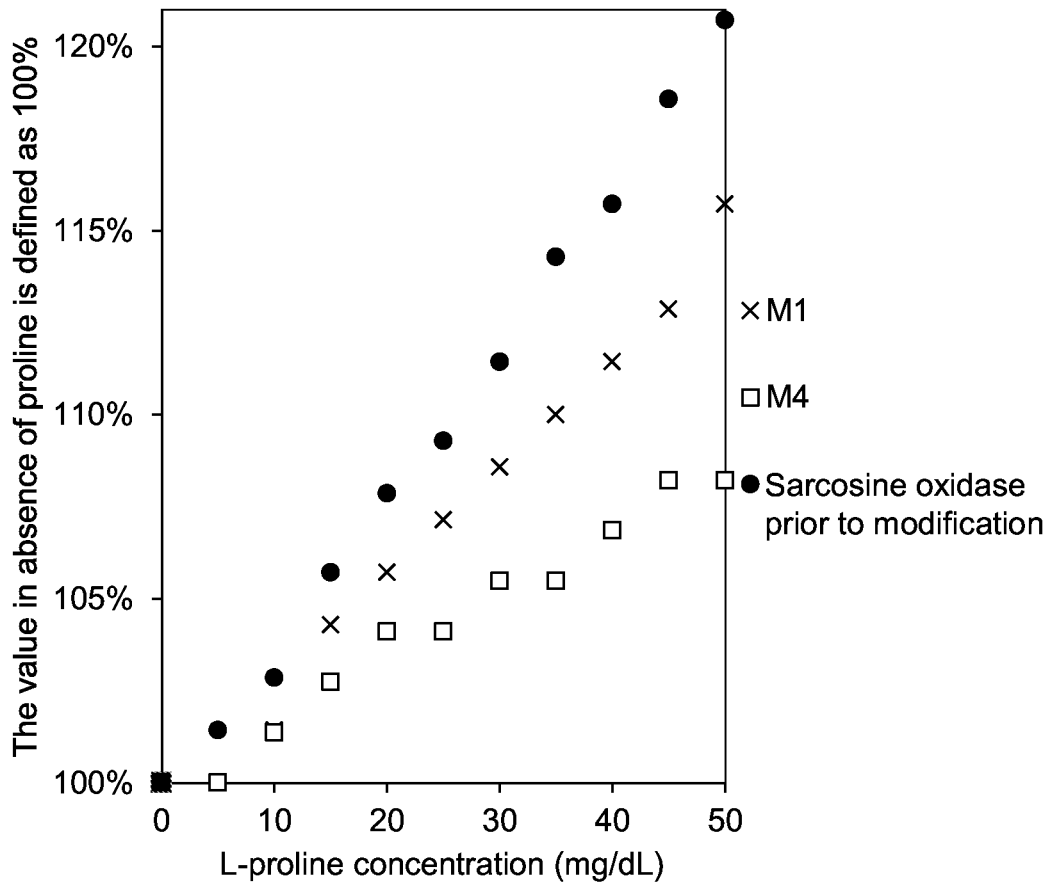
FIG. 4 shows effects of proline on modified sarcosine oxidases and a sarcosine oxidase prior to modification (serum: EXA Liquid 3 normal).
Figure 5:
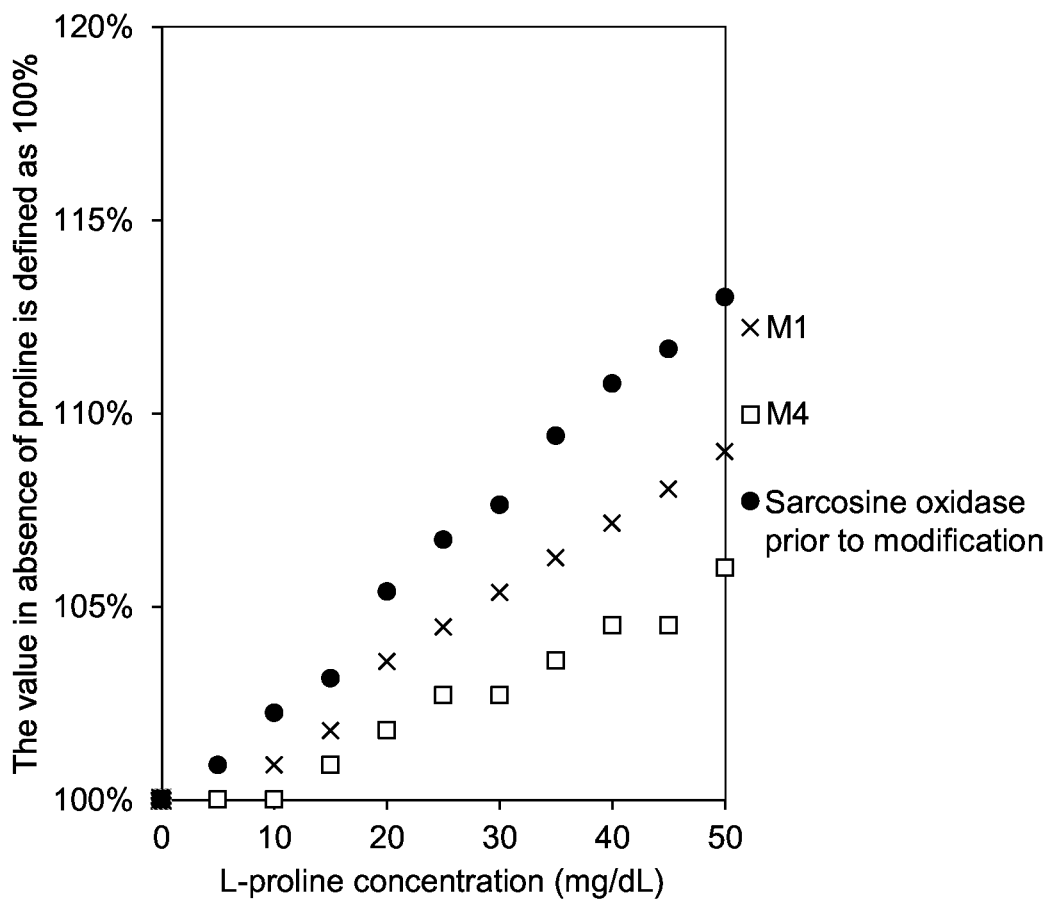
FIG. 5 shows effects of proline on modified sarcosine oxidases and a sarcosine oxidase prior to modification (serum: Seiken Liquid Normal V).

As a result, reactivity of M4 to proline was not only lower than that of the sarcosine oxidase prior to modification but also reactivity of M4 to proline was lower than that of M1 (FIGS. 3 to 5).

Incidentally, when reactivity to 5.0 mg/dL of creatinine was compared between a reagent using the modified sarcosine oxidase M4 and reagent using the sarcosine oxidase prior to modification (SEQ ID NO: 1), the reactivities before and after modification were the same. It, therefore, was found that the reaction of the modified sarcosine oxidase M4 was the same as that of the sarcosine oxidase prior to modification, and the effect of proline on M4 is suppressed.

Brief Description of Sequences

SEQ ID NO: 1: Wild-type sarcosine oxidase from *Bacillus* NS-129
SEQ ID NO: 2: Modified sarcosine oxidase M1 (K320N/E324G/Y222H/F348Y/A314S)
SEQ ID NO: 3: Modified sarcosine oxidase M2 (K320N/E324G/F260I)
SEQ ID NO: 4: Modified sarcosine oxidase M3 (K320N/E324G/F260I/Y222A)
SEQ ID NO: 5: N-Terminus side sequence for error-prone PCR atgagcacgcattttgacgta
SEQ ID NO: 6: C-Terminus side sequence for error-prone PCR ttattttactgcttctttttttaatgcatc
SEQ ID NO: 7 to 21: Primers for introducing mutations
SEQ ID NO: 22: Modified sarcosine oxidase M4 (K320N/E324G/Y222H/A314S/F343G)
SEQ ID NO: 23 to 24: Primers for introducing mutations All publications, patents and patent applications referred to in the present specification are incorporated by reference into the present specification in their entirety.

The invention claimed is:

1. A modified sarcosine oxidase wherein said modified sarcosine oxidase is a protein comprising an amino acid sequence having 80% or more identity with the amino acid sequence of SEQ ID NO: 2, 3, or 4, wherein, with regard to said protein, the amino acid at the position corresponding to position 320 in SEQ ID NO: 1 is asparagine and the amino acid at the position corresponding to position 324 in SEQ ID NO: 1 is glycine, said protein having sarcosine oxidase activity with reduced reactivity to L-proline compared to that of a protein having a sequence identical to SEQ ID NO: 1.

2. The modified sarcosine oxidase of claim 1, wherein the amino acid at the position corresponding to position 348 in SEQ ID NO: 1 is tyrosine.

3. The modified sarcosine oxidase of claim 1, wherein the amino acid at the position corresponding to position 222 in SEQ ID NO: 1 is alanine or histidine.

4. The modified sarcosine oxidase of claim 1, wherein the amino acid at the position corresponding to position 260 in SEQ ID NO: 1 is isoleucine.

5. The modified sarcosine oxidase of claim 1, wherein the amino acid at the position corresponding to position 314 in SEQ ID NO: 1 is serine.

6. The modified sarcosine oxidase of claim 1, wherein the amino acid at the position corresponding to position 343 in SEQ ID NO: 1 is glycine.

7. A creatinine measurement reagent comprising the modified sarcosine oxidase of claim 1.

8. A method for measuring creatinine comprising a step of contacting the modified sarcosine oxidase of claim 1 with a sample which may contain sarcosine or a sample wherein sarcosine may be produced by the action of an enzyme.

* * * * *